United States Patent
Couston et al.

(10) Patent No.: US 7,180,589 B2
(45) Date of Patent: Feb. 20, 2007

(54) LUMINESCENCE MEASURING DEVICE WITH PRE-FILTER EFFECT SUPPRESSION

(75) Inventors: Laurent Couston, les Angles (FR); Jacques Delage, Orange (FR)

(73) Assignee: Commissariat a l'Energie Atomique, Paris (FR)

( * ) Notice: Subject to any disclaimer, the term of this patent is extended or adjusted under 35 U.S.C. 154(b) by 383 days.

(21) Appl. No.: 10/474,207

(22) PCT Filed: Apr. 25, 2002

(86) PCT No.: PCT/FR02/01425

§ 371 (c)(1),
(2), (4) Date: Oct. 20, 2003

(87) PCT Pub. No.: WO02/088685

PCT Pub. Date: Nov. 7, 2002

(65) Prior Publication Data

US 2004/0130716 A1    Jul. 8, 2004

(30) Foreign Application Priority Data

Apr. 27, 2001  (FR) .................................. 01 05710

(51) Int. Cl.
*G01J 3/30* (2006.01)
(52) U.S. Cl. .................................................. 356/318
(58) Field of Classification Search ......... 356/317–318
See application file for complete search history.

(56) References Cited

U.S. PATENT DOCUMENTS 5,905,570 A * 5/1999 White et al. ................. 356/317

6,327,489 B1 * 12/2001 Hoogenraad et al. ....... 356/432
6,707,548 B2 * 3/2004 Kreimer et al. ............. 356/301
2001/0046045 A1 * 11/2001 Dong et al. ................. 356/317

OTHER PUBLICATIONS

McYappert et al.: "Correction of polychromatic luminescence signals for inner-filter effects" Applied Spectroscopy, the Society for Applied Spectroscopy, vol. 43, No. 5, pp. 759-767 Jul. 1, 1989.
T. Berthoud et al.: " Direct uranium trace analysis in plutonium solutions by time-resolved laser-induced spectrofluorometry" Analytical Chemistry, vol. 60, No. 13 pp. 1296-1299, Jul. 1, 1988.
Matsui Tetsuya et al.: "A correction method for fluorescence by reduction using time-resolved fluorometry and spectrophotometry" Applied Spectroscopy, the Society for Applied Spectroscopy, vol. 45, No. 1, pp. 32-35, 1991.
Sa Siano: "Deconvolution of multicomponent fluorescence spectra in the presence of absorption inner-filter effects" Journal of Quantitative Spectroscopy and Radiative Transfer, vol. 47, No. 1 pp. 55-73, Jan. 1992.

* cited by examiner

*Primary Examiner*—Gregory J. Toatley, Jr.
*Assistant Examiner*—Kara Geisel
(74) *Attorney, Agent, or Firm*—Oblon, Spivak, McClelland, Maier & Neustadt, P.C.

(57) ABSTRACT

A device for measuring the intensity of a luminescence radiation emitted by at least one chemical species probed, along a trajectory by an excitation radiation. The device includes n measurement channels, where n is an integer greater than or equal to 2, each measurement channel being used to measure a fraction of the intensity of the luminescence radiation emitted along the trajectory. The device is also applicable to analytical chemistry to make speciation measurements.

5 Claims, 2 Drawing Sheets

LUMINESCENCE MEASURING DEVICE WITH PRE-FILTER EFFECT SUPPRESSION

TECHNICAL DOMAIN AND PRIOR ART

The invention relates to a luminescence measurement device.

More particularly, the invention relates to a luminescence measurement device with elimination of the pre-filter effect.

A luminescence (fluorescence or phosphorescence) measurement device comprises means of exciting a chemical species by electromagnetic radiation for which the wavelength is tuned to one of the electrical transitions of the chemical species, optical means for collecting and diffracting the emitted luminescence radiation and means of measuring the intensity of the luminescence spectrum.

A principle diagram for a luminescence measurement device is shown in FIG. 1. A measurement cell 2 contains a chemical species 3. An excitation radiation 1 passes through the measurement cell 2. The luminescence radiation emitted in direction approximately perpendicular to the axis of the excitation beam 1 is collected on an optical lens 4 and is focused on a spectrometer 5. An optical sensor 6 converts the focussed radiation into an electrical signal. The locally probed solution fraction has a range $d_{AB}$ and is located at a depth $d_{OA}$ inside the cell 2. The luminescence radiation emitted in the direction approximately perpendicular to the axis of the excitation beam passes a distance L in the tank 2 before reaching the optical lens 4.

The emitted radiation intensity is proportional to the low concentration of the luminescent species.

This type of luminescence measurement is used, for example, in analytic chemistry. The measurement sensitivity can then be used to carry out very low level analyses and to make speciation studies.

The chemical species subjected to radiation is composed of a luminophore diluted in a medium.

The luminophore dilution medium can induce physical interactions that result in a modification of the intensity of the relaxation spectrum. Three physical interactions are particularly severe. One first interaction relates to variations in the deactivation velocity due to the transfer of energy or electrons between the excited species and an inhibitor. The efficiency of this deactivation depends on the nature and concentration of the inhibiting species (Stern-Volmer's law). A second interaction relates to partial absorption of the energy of the source by the medium probed along the direction of the excitation beam (pre-filter effect). This absorption may be induced either by specific absorbance of the dilution medium, or by absorbance of the highly concentrated luminophore (self-induced pre-filter effect). A third interaction relates to the absorption of luminescence radiation by the medium along the direction approximately perpendicular to the direction of the excitation beam (post-filter effect).

The pre-filter and post-filter effects, more usually called internal filter effects, result in a loss of signal related to the chemical composition of the medium (matrix effect).

The presence of these three effects frequently leads to the need for a chemical treatment of the sample before measuring the fluorescence (dilution/change of matrix). Luminescence techniques are then unsuitable for in-line analysis.

The effects of internal filters have been studied theoretically in order to model the measured signal. For example, this is the case in the document entitled "*Correction of Polychromatic Luminescence signals for Inner-filter Effects*" by M. Cecilia YAPPERT and J D INGLE, J. R. appeared in the APPLIED SPECTROSCOPY journal, vol. 43, number 5, 1989. It is also the case in the document entitled "*Direct Uranium Trace Analysis in Plutonium Solutions by Time-Resolved Laser-Induced Spectrofluorometry*" by Thierry Berthoud, Pierre Decambox, Barbara Kirsch, Patrick Mauchien and Christophe Moulin, published in the ANALYTICAL CHEMISTRY journal, vol. 60, No. 13, Jul. 1, 1988.

The latter document describes how to deduce the fluorescence intensity expression measured in the presence of inner filters. It is written:

$$F_{measured} = I_0 \cdot F_1 \cdot F_2 \cdot K \cdot f(C_M, t_{irr})$$

where
$I_0$ is the excitation radiation intensity at the tank inlet,
$F_1$ is a coefficient related to the pre-filter effect,
$F_2$ is a coefficient related to the post-filter effect,
K is a device constant,
$f(C_M, t_{irr})$ is the theoretical expression of the fluorescence intensity for a given irradiation time $t_{irr}$. It is linearly related to the concentration $C_M$ of the luminescent species M and it is defined by parameters through its spectroscopic constants $\phi_M$ (quantum efficiency) and $\epsilon_M$ (molar extinction coefficient).
The coefficient $F_1$ is written:

$$F1 = \left[ e^{-\Sigma_i \epsilon_i^{exc} \cdot d_{OA} \cdot C_i} \right] \cdot \left[ \frac{1 - e^{-\Sigma_i \epsilon_i^{exc} \cdot d_{AB} \cdot C_i}}{\sum_i \epsilon_i^{exc} \cdot d_{AB} \cdot C_i} \right]$$

where
$\epsilon_i^{exc}$ is the molar extinction coefficient of the species i at the excitation wavelength,
$C_i$ is the concentration of species i,
$d_{OA}$ is the depth at which the locally probed zone is located (see FIG. 1),
$d_{AB}$ is the total distance over which the chemical species is locally probed (see FIG. 1).
The coefficient $F_2$ is written:

$$F_2 = \left[ e^{-\Sigma_j \epsilon_j^{em} \cdot L \cdot Cj} \right]$$

Where
$\epsilon_j^{em}$ is the molar extinction coefficient of species j at the luminescence emission wavelength,
L is the distance travelled in the tank by the luminescence radiation emitted perpendicular to the axis of the excitation beam (see FIG. 1),
Cj is the concentration of species j. According to known art, the pre-filter effects are treated in one of the following manners:
either by firstly measuring the absorbance of the medium at the excitation wavelength,
or by measuring the intensity transmitted by the source at the end of its path through the tank, using another measurement system,
or by using sequential fluorescence measurements related to relative displacements of the detection optics and the measurement cell.

These various measurement types are expensive both in terms of time and equipment. They are not applicable to in-line analysis, and furthermore they increase the dispersion of analyses by successive measurements of imperfectly correlated events.

The invention does not have these disadvantages.

Presentation of the Invention

The invention relates to a device for measuring the intensity of luminescence radiation emitted by at least a chemical species probed, along a trajectory by an excitation radiation. The device comprises n measurement channels, where n is an integer equal to or greater than 2, each measurement channel being used to measure a fraction of the intensity of the luminescence radiation emitted along the trajectory.

Advantageously, the measurement device according to the invention enables correction of the pre-filter effect in real time. Data characterizing the pre-filter effect are acquired without prior diagnostic of the medium and without relative mobility of the detection optics and the sample. The technique based on spatial sampling of the luminescence emission is also transposable to the in situ analysis offset by optode.

BRIEF DESCRIPTION OF THE FIGURES

Other characteristics and advantages of the invention will become clearer after reading a preferred embodiment of the invention described with reference to the attached figures among which.

The same marks denote the same elements in all figures.

DETAILED DESCRIPTION OF AN EMBODIMENT OF THE INVENTION

Figure 1:
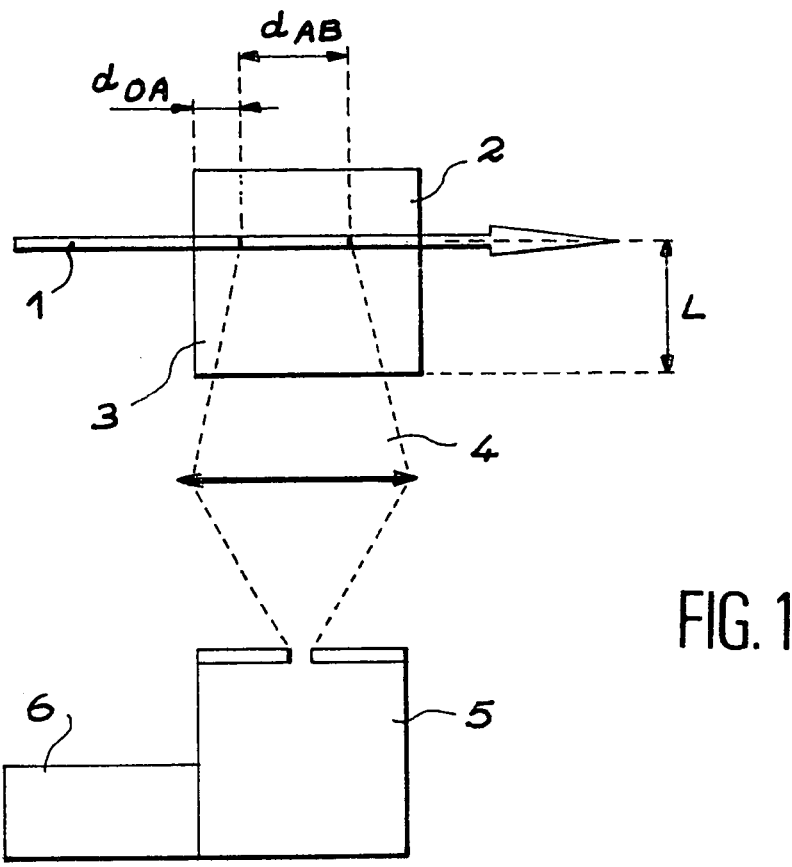
FIG. 1 shows a luminescence measurement device according to prior art.

FIG. 1 has already been described above, therefore there is no point in describing it again.

Figure 2:
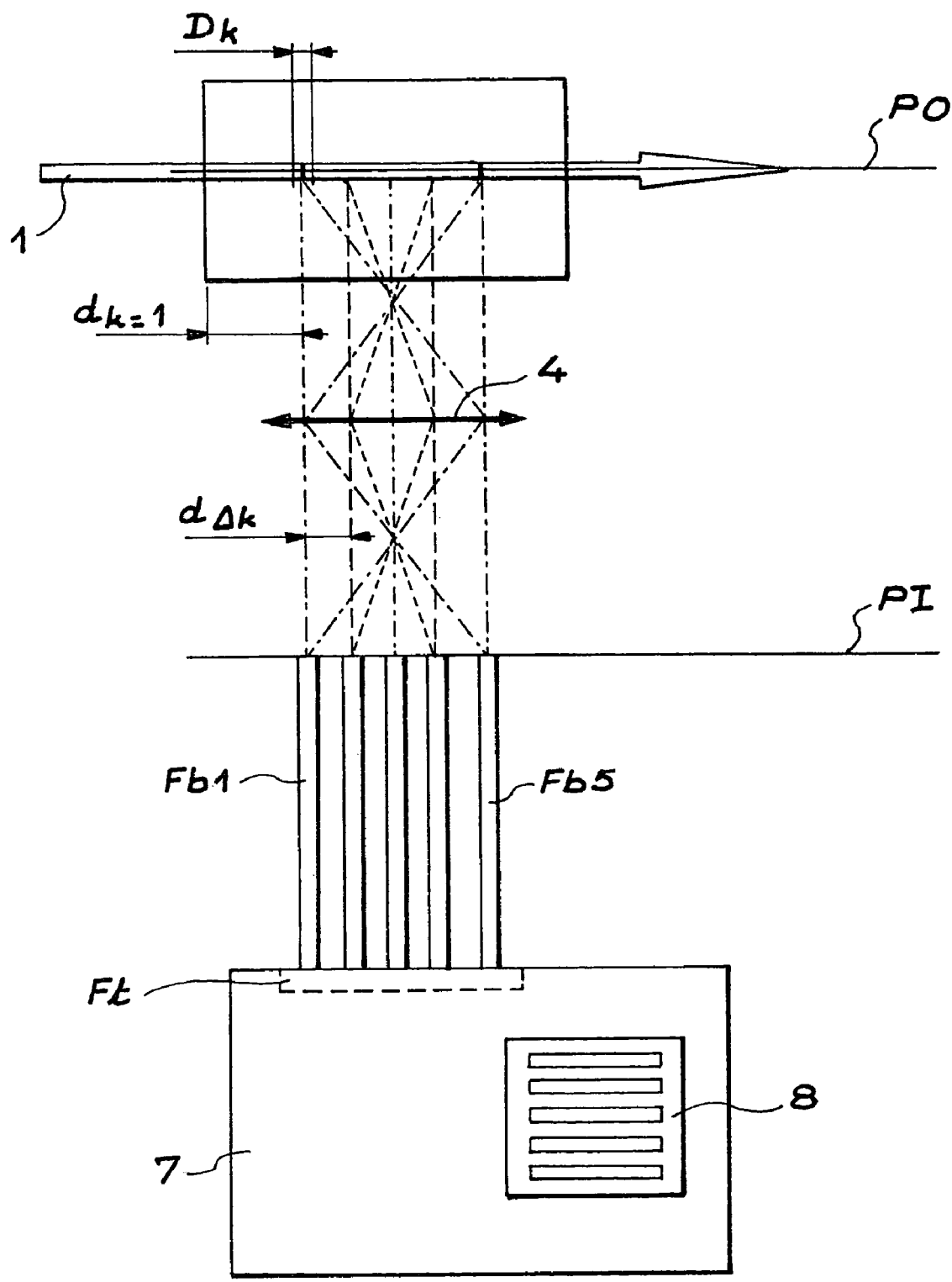
FIG. 2 shows a luminescence measurement device according to the invention.

FIG. 2 shows a luminescence measurement device according to the invention. The measurement device comprises an optical lens 4 preferably installed in double focus (2f), a set of n optical fibres Fbi (5 optical fibres are shown in FIG. 2 as a non-limitative example) and a plane field spectrometer 7.

An assembly type other than the double focus optical assembly may also be used, but there would then be the disadvantage that the system could not be easily calibrated.

The excitation radiation 1 passes through the measurement cell 2. The luminescence radiation emitted in the direction approximately perpendicular to the beam axis is collected on the optical lens 4. The chemical species is probed along a trajectory located in the object plane PO of the lens. The number of n of optical fibres is equal to at least 2. Each optical fibre collects a fraction of the luminescence image at a first of its ends. The first ends of n optical fibres are aligned in the image plane PI of the lens. At their other end, the n optical fibres are aligned with the same arrangement, on an inlet slit Ft of the spectrometer 7 so as to form n measurement channels. The spectrometer 7 individually and simultaneously diffracts each measurement channel. The weakening of the signal in successive measurement zones at a given luminescence wavelength provides a means of deducing the value of the absorbance ($\Sigma \epsilon_i C_i$) and of calculating an attenuation factor of the intensity measured along the probed trajectory.

The attenuation factor of the pre-filter is $\Omega_k$, such that:

$$\Omega_k = \left[ e^{-\Sigma_i \epsilon_i^{exc} \cdot (d_{k=1} + (k-1)d_{\Delta k}) \cdot C_i} \right] \cdot \left[ \frac{1 - e^{-\Sigma_i \epsilon_i^{exc} \cdot D_k \cdot C_i}}{\sum_i \epsilon_i^{exc} \cdot D_k \cdot C_i} \right] k \leq n, \quad (2)$$

where:
k is the rank of the fibre along the direction of the probed trajectory,
$\epsilon_i^{exc}$ is the molar extinction coefficient of species i at the excitation wavelength,
$C_i$ is the concentration of species i,
$d_{k=1}$ is the distance travelled in the solution by the excitation radiation before it reaches the first fibre,
$d_{\Delta k}$ is the distance between two successive fibres,
$D_k$ is the distance over which the chemical species is locally probed, and that corresponds to the radiation fraction collected by the rank k fibre.

The values of the distances $d_{k=1}$, $d_{\Delta k}$ and $D_k$ are either deduced from the mechanical assembly of the measurement device, or calibrated after measuring the luminescence of the reference samples.

The measured luminescence intensity fractions corrected for pre-filter effects can then be added and used, for example for analytic purposes.

Apart from the advantages of accessing an analytic measurement in an absorbent medium without preparation of the sample, the measurement method according to the invention also has the following other advantages:

it is adapted to conventional fluorometry (continuous source) or to time resolution fluorometry (pulsed source), it is independent of variations in the energy of the excitation source, it does not require that the nature and molar extinction coefficient of the species responsible for the pre-filter effect have to be known, it increases the range of the fluorometry analysis by elimination of the self-induced pre-filter effect (the measurement range only depends on the acquisition system, such that this range can be improved by several decades), it enables the luminophore and the species responsible for the pre-filter effect to be analysed simultaneously, it can be transposed to in-line analysis by adding an additional detection channel to currently marketed fluorometry optodes.

Taken as a whole, the measurement system according to the invention is composed of an assembly of the following elements:

a monochromatic light source (pulsed or continuous, of the lamp or laser type) designed to excite the luminophore species, a measurement cell or an optode intended for spatial sampling of luminescence, a plane field spectrometer that can be equipped with a multiple channel detector (CCD camera or photodiode module), acquisition electronics, and a computer.

Independent measurements carried out simultaneously on n measurement channels require the use of multichannel optical sensors (Charge Coupled Devices) that have the advantage of selectively measuring the fluorescence spectrum transmitted by the n optical fibres. Thus, it provides all necessary information. A photodiodes module fixed perpendicular to the optical dispersion axis of the spectrometer can also be used to selectively measure the fluorescence intensity transmitted by the n fibres at the chosen wavelength. The spectrometer can be simultaneous (polychromator) or sequential with wavelength scanning to access the fluorescence spectrum.

The best performances of the measurement and correction system according to the invention are obtained if some conditions are respected. Thus, the optical fibres preferably all have the same nature and the same dimensions in order to simplify management of specific absorptions and to prevent multiplication of the number of geometric constants. The diameter of the optical fibres Fbi and the focal distance of the probe lens 4 are preferably calculated such that the image of the luminescence "line" (geometry of the luminescence line multiplied by the magnification of the optical system) is optimally superposed on the arrangement of optical fibres. Also, radiation is transmitted from the source to the measurement cell preferably by collimating the beam such that the medium refraction index does not modify the geometry of the luminescence "line" on the length interval separating areas probed by the first and the $n^{th}$ fibres.

The correction precision is greater when the number of optical fibres is larger.

The distances $d_{k=1}$, $d_{\Delta k}$ and $D_k$ can be evaluated from the mechanical planes and the optical characteristics of the assembly. However, a more precise characterization started from reference samples is preferable. Reference solutions are necessarily made by diluting a luminophore in media with known absorbances at the excitation wavelength. Among these solutions, the solution using a luminophore diluted in a medium with zero absorbance firstly makes it possible to check the equity of the response of n measurement channels, or if applicable to determine the values of n instrument local constants to achieve this response equity. They depend exclusively on the quality of the lenses and the surface conditions of the fibres, and the only way that they can change with time is by dirt accumulation.

Then, reference solutions with non-zero absorbances at the excitation wavelength are probed by the n measurement channels. The parameters $d_{k=1}$, $d_{\Delta k}$ and $D_k$ are then deduced by adjusting the expression 2 (see page 8) to all experimental data.

As a non-limitative example, a system used according to the invention is composed of:

a measurement tank with a 1 cm square side, an optical probe lens with a focal distance f=7 cm, arranged in a 2f assembly (double focus/optical magnification of 1), an optical alignment or optical pen with eight optical fibres with a 260 μm core uniformly distributed on a 6 mm long segment, a source focusing lens in the medium.

The condition for local collimation of light is respected by using a lens with a long focal length (for example f=300 mm) compared with the distance of 6 mm theoretically probed between fibres 1 and 8.

The calibration of the detection system and its performances will now be described to validate the function of the device: hexavalent uranium is used as the luminescent species. Its concentration is adjusted to $4\times10^{-3}$ mol/L in four nitric acid solutions with concentrations 0.1, 1.1, 2.5 and 3.4 mol/L.

Two excitation wavelength are used to qualify the method:

the wavelength of 337 nm for which the excitation efficiency of uranium is high and the molar extinction coefficient of nitric acid (0.2 $mol^{-1}.cm^{-1}$) induces sensitive pre-filter effects for concentrations of more than 0.5 $mol.L^{-3}$, the wavelength of 355 nm for which the excitation efficiency of uranium is about eight times lower than the excitation efficiency for the 337 nm wavelength and the molar extinction coefficient of nitric acid is negligible (0.015 $mol^{-1}.cm^{-1}$).

The nitrate ion added by nitric acid reacts with free uranium (in $UO_2^{2+}$ form) to form the $UO_2(NO_3)^+$ and $UO_2(NO_3)_2$ species. The concentration of uranyl nitrate increases as the concentration of $HNO_3$ increases. However, the low reactivity of nitrate ions is not sufficient to change the equilibriums completely, which explains the fact that free and nitrated forms of uranyl are present simultaneously.

At 514 nm, the emission wavelength of uranium, the increase in the concentration of nitric acid results in an increase in the fluorescence efficiency related to the highest quantum efficiency of the $UO_2(NO_3)^+$ and $UO_2(NO_3)_2$ species. This property, known in spectroscopy, is independent of the excitation wavelength.

The increase in the fluorescence signal is directly measurable at $\lambda_{exc}$=355 nm.

It is not measurable at $\lambda_{exc}$=337 nm, due to competition with the pre-filter effect.

Table 1 below shows the local fluorescence intensities measured by the eight optical channels at excitation wavelengths 337 and 355 nm on uranium solutions at $4.10^{-3}$ mol/L:

TABLE 1

| $\lambda_{exc}$ | [$HNO_3$] | Fibre 1 | Fibre 2 | Fibre 3 | Fibre 4 | Fibre 5 | Fibre 6 | Fibre 7 | Fibre 8 |
|---|---|---|---|---|---|---|---|---|---|
| 337 nm | 0.1 | 5322 | 5362 | 5317 | 5480 | 5438 | 5273 | 5260 | 5077 |
|  | 1.1 | 9451 | 9435 | 9059 | 9241 | 9001 | 8680 | 8660 | 9113 |
|  | 2.5 | 11154 | 11101 | 10191 | 9937 | 9141 | 8358 | 8082 | 8256 |
|  | 3.4 | 11340 | 13464 | 10004 | 9729 | 8998 | 8297 | 7828 | 7620 |

TABLE 1-continued

| $\lambda_{exc}$ | [HNO$_3$] | Fibre 1 | Fibre 2 | Fibre 3 | Fibre 4 | Fibre 5 | Fibre 6 | Fibre 7 | Fibre 8 |
|---|---|---|---|---|---|---|---|---|---|
| 355 nm | 0.1 | 2180 | 2145 | 2142 | 2150 | 2180 | 2192 | 2199 | 2180 |
|  | 1.1 | 4382 | 4348 | 4405 | 4384 | 4461 | 4271 | 4143 | 4440 |
|  | 2.5 | 5054 | 5098 | 5108 | 5110 | 4980 | 5021 | 5131 | 5010 |
|  | 3.4 | 5544 | 5629 | 5555 | 5558 | 5526 | 5695 | 5737 | 5517 |

Determination of Instrument Local Constants

The search for instrument local constants (specific to each measurement channel) consists of normalizing the fluorescence intensity collected by the eight optical fibres in a non-absorbent medium ($\lambda_{exc}$=355 nm).

They are given in Table 2 below:

TABLE 2

| $\lambda_{exc}$ | Channel 1 | Channel 2 | Channel 3 | Channel 4 | Channel 5 | Channel 6 | Channel 7 | Channel 8 |
|---|---|---|---|---|---|---|---|---|
| 355 | 1.0 | 0.91 | 0.87 | 0.88 | 0.90 | 0.90 | 0.96 | 1.22 |

The identified measurements in Table 1 are corrected by instrument local constants in the remainder of the description.

The characteristic constants of the optical device are:
the distance travelled in the solution by the light source before reaching the first local fluorescence zone, $d_{k=1}$,
the distance that separates two successive local fluorescence zones, $d_{\Delta k}$,
the length of the local fluorescence zone $D_k$.

Determination of the Constant Dk

The magnification for a probe lens in double focus assembly is approximately 1. Consequently, each optical fibre locally probes the fluorescence line over a distance corresponding approximately to its core diameter (0.026 cm). Experimental conditions are then such that the term $\epsilon_i^{exc} D_k . C_i$ is between $5 \times 10^{-4}$ and 0.02. Therefore, the second factor in expression 2 relates to less than 1% of the final result. Therefore, it cannot be measured by this calibration so that it is necessary to force the constant $D_k$ to the theoretical value of 0.026 cm. A value of at least 10 times greater than the term $\epsilon_i^{exc} D_k . C_i$ is preferable to determine the constant $D_k$ by calibration.

However, precise knowledge of the term $D_k$ is not very important compared with the importance of the constants $d_{k=1}$ and $d_{\Delta k}$.

Determination of Constants $d_{k=1}$ and $d_{\Delta k}$:

At $\lambda_{exc}$=337 nm, the attenuation of the local fluorescence intensity measured by the eight successive fibres is adjusted by the model deduced from expressions (1) and (2):

$$F_k^{exp} = I_0 \cdot \Omega_k \cdot C_M = F_M \cdot \left[ e^{-\Sigma_i \epsilon_i^{exc} \cdot (d_{k=1}+(k-1)d_{\Delta_k}) \cdot C_i} \right], \quad (3)$$

If the absorbance of nitric acid at 337 nm is known, the best adjustment of equation 3 to attenuations of fluorescence intensities measured at acidities of 0.1 mol.L$^{-1}$, 1.1 mol.L$^{-1}$, 2.5 mol.L$^{-1}$ and 3.4 mol.L$^{-1}$ gives the following distance constants:

$d_{k=1}$=0.139 cm $d_{\Delta k}$=0.081 cm

The value $d_{\Delta k}$=0.081 cm agrees well with the value of 0.085 that could have been deduced theoretically from the geometry of the optical pen combined with the probe lens in 2f assembly. It validates the assumption made for the magnification 1 of the optical device and the value of the constant $D_k$=0.026 cm that is deduced from it.

The local values of fluorescence intensity measured at the excitation wavelength of 0.337 nm are corrected by instrument local constants and pre-filter effects.

They are added and compared to the sum of local fluorescence intensities measured at the excitation wavelength of 355 nm, corrected by instrument local constants.

Figure 3:
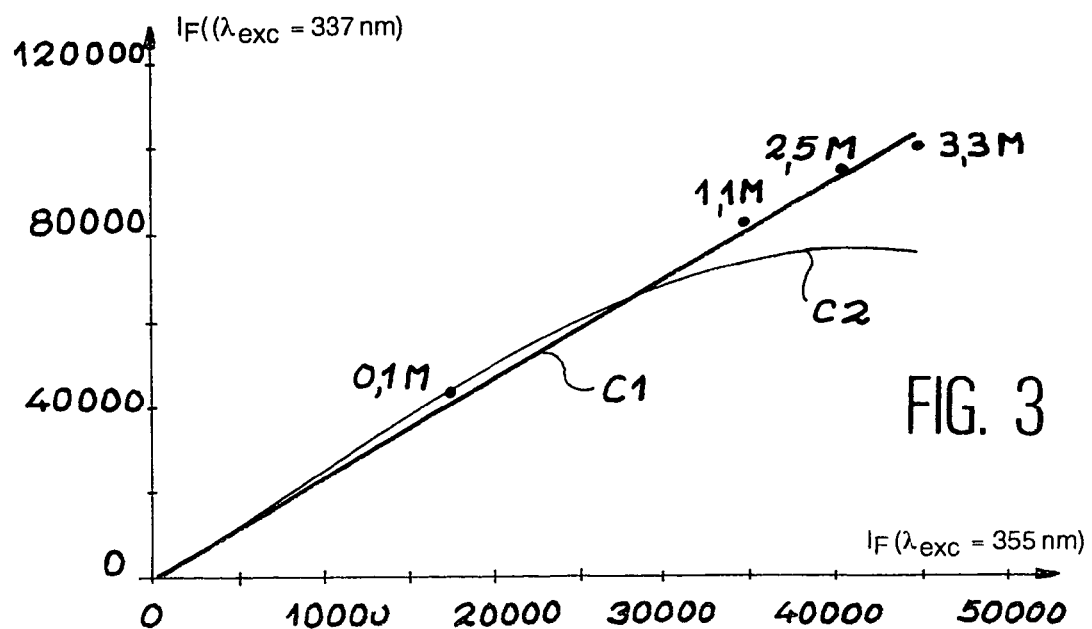
FIG. 3 shows a comparison between values of the measured intensity of the luminescence radiation obtained with and without correction of the pre-filter effect.

FIG. 3 shows a comparison between values of intensity measurements of the luminescence radiation obtained with and without a pre-filter effect correction.

The curves in FIG. 3 show the efficiency of the method to correct the pre-filter effects. Fluorescence intensities $I_F$ of uranium in water or in a nitric medium with a low concentration are compared, for four concentration values (0.1 mol.L$^{-1}$, 1.1 mol.L$^{-1}$, 2.5 mol.L$^{-1}$ and 3.3 mol.L$^{-1}$) after excitation at 337 nm and at 355 nm. Curve C1 represents the curve of experimental values corrected for pre-filter effects, and curve C2 represents the curve of uncorrected experimental values. The slope of curve C1 is explained partly by the difference in laser energy and partly by the difference in the fluorescence efficiency of uranium at wavelengths 337 and 355 nm.

The invention is also applicable to determination of the fluorescence intensity of a solution of uranium in a nitric medium with an unknown concentration.

Table 3 below gives the local fluorescence intensities of a solution of uranium at $4 \times 10^{-3}$ mol.L not titrated in nitric acid:

TABLE 3

| $\lambda_{exc}$ | [HNO$_3$] | Fibre 1 | Fibre 2 | Fibre 3 | Fibre 4 | Fibre 5 | Fibre 6 | Fibre 7 | Fibre 8 |
|---|---|---|---|---|---|---|---|---|---|
| 337 nm | / | 13946 | 14791 | 14329 | 13416 | 12000 | 10779 | 9534 | 7279 |

The experimental values are corrected by instrument local constants and are then adjusted using equation (2), in which the distance constants have been characterized.

Knowledge of all parameters of the equation provides a means of correcting the pre-filter effect and deducing a total fluorescence intensity of 132792 UA. This value is quite comparable with the value 58242 measured at $\lambda_{exc}$=355 nm (the difference being a factor of 2.3).

Apart from correction of the pre-filter effect, the value $\epsilon C$ related to the presence of nitric acid alone allows the solution to be titrated at 4.4 mol.L$^{-1}$, while with acid-base titration the measured value is 4.61 mol.L$^{-1}$.

Therefore, the pre-filter effect is properly corrected, and the fluorescence intensity of uranium solutions only depends on the concentration of uranium in its various complex forms.

The invention claimed is:

1. A device for measuring intensity of a luminescence radiation emitted by at least one chemical species probed along a trajectory by an excitation radiation, comprising:
    n measurement channels, where n is an integer greater than or equal to 2, each measurement channel configured to measure a fraction of the intensity of the luminescence radiation emitted along the trajectory; and
    an optical lens configured such that the trajectory along which the chemical species is probed is located in an object plane of the lens and such that each measuring channel comprises an optical fiber with a first end, the first ends of the n optical fibers being aligned in an image plane of the lens, so that each optical fiber collects a fraction of the luminescence radiation, wherein
    the optical lens is assembled in double focus.

2. A device for measuring intensity of a luminescence radiation emitted by at least one chemical species probed along a trajectory by an excitation radiation, comprising:
    n measurement channels, where n is an integer greater than or equal to 2, each measurement channel configured to measure a fraction of the intensity of the luminescence radiation emitted along the trajectory; and
    an optical lens configured such that the trajectory along which the chemical species is probed is located in an object plane of the lens and such that each measuring channel comprises an optical fiber with a first end, the first ends of the n optical fibers being aligned in an image plane of the lens, so that each optical fiber collects a fraction of the luminescence radiation, wherein
    each optical fiber has a second end, and the second ends of the n optical fibers are aligned along an inlet slit of a plane field spectrometer.

3. Measuring device according to claim 2, further comprising one of a CCD sensor and a photodiode module configured to measure the intensities of different fractions of luminescent radiation output from the spectrometer.

4. Measuring device according to claim 2, wherein the spectrometer is one of a simultaneous spectrometer and a sequential spectrometer with wavelength scanning.

5. A device for measuring intensity of a luminescence radiation emitted by at least one chemical species probed along a trajectory by an excitation radiation, comprising:
    n measurement channels, where n is an integer greater than or equal to 2, each measurement channel configured to measure a fraction of the intensity of the luminescence radiation emitted along the trajectory; and
    an optical lens configured such that the trajectory along which the chemical species is probed is located in an object plane of the lens and such that each measuring channel comprises an optical fiber with a first end, the first ends of the n optical fibers being aligned in an image plane of the lens, so that each optical fiber collects a fraction of the luminescence radiation, wherein the attenuation factor is such that:

$$\Omega_k = \left[ e^{-\Sigma_i \varepsilon_i^{exc} \cdot (d_{k=1} + (k-1)d_{\Delta_k}) \cdot C_i} \right] \cdot \left[ \frac{1 - e^{-\Sigma_i \varepsilon_i^{exc} \cdot D_k \cdot C_i}}{\sum_i \varepsilon_i^{exc} \cdot D_k \cdot C_i} \right] k \leq n, \quad (2)$$

where:

k is rank of the optical fiber along a direction of the probed trajectory, $d_{k=1}$ is distance travelled in solution by the excitation radiation before it reaches a first of the optical fibers, $d_{\Delta k}$ is distance between two successive optical fibers, $D_k$ is distance over which the chemical species is locally probed, and that corresponds to the radiation fraction collected by the rank k optical fiber, $\epsilon_i^{exc}$ is molar extinction coefficient of the chemical species i at an excitation wavelength, and $C_i$ is concentration of the chemical species i absorbent at the excitation wavelength.

* * * * *